| United States Patent [19] | [11] 4,067,997 |
|---|---|
| Kabara | [45] Jan. 10, 1978 |

[54] SYNERGISTIC MICROBECIDAL COMPOSITION AND METHOD

[75] Inventor: Jon J. Kabara, Okemos, Mich.

[73] Assignee: Med-Chem Laboratories, Okemos, Mich.

[21] Appl. No.: 749,110

[22] Filed: Dec. 9, 1976

Related U.S. Application Data

[63] Continuation-in-part of Ser. No. 579,687, May 21, 1975, Pat. No. 4,002,775, which is a continuation-in-part of Ser. No. 377,187, July 9, 1973, abandoned.

[51] Int. Cl.² .................... A61K 31/23; A61K 31/22; A61K 31/05
[52] U.S. Cl. ...................................... 424/312; 424/49; 424/314; 424/346; 426/335
[58] Field of Search ................... 424/312, 314, 346, 49

[56] References Cited

PUBLICATIONS

Chem. Abst., 8th Coll. Index, vol. 66–75, (1967–1971), p. 17308s.

*Primary Examiner*—Sam Rosen
*Attorney, Agent, or Firm*—Murray & Whisenhunt

[57] ABSTRACT

There is provided a microbecidal or microbiostatic water-dispersible synergistic combination of a non-ionic surface-active agent that is a mono-ester of a twelve carbon atom aliphatic acid and a polyol and at least one microbecide, e.g., a phenolic compound (including resorcinol compounds). Preferably, the weight ratios of the microbecide-to-ester are between 1:1 to 1:100. These compositions may be dispersed in water and avoid inactivation of the microbecide. Further, the present composition provides activity greater than either the ester or the microbecide alone.

34 Claims, 3 Drawing Figures

SYNERGISTIC MICROBECIDAL COMPOSITION AND METHOD

This is a continuation-in-part of copending application Ser. No. 579,687, filed on May 21, 1975, now U.S. Pat. No. 4,002,775, which application is in turn a continuation-in-part of Ser. No. 377,187, filed on July 9, 1973, now abandoned.

The present invention relates to compositions containing non-ionic surface-active aliphatic 12 carbon atom acid-polyol mono-esters in combination with a microbecide. More particularly, the invention relates to such compositions which avoid the prior art problems of non-ionic surface-active agents inactivating microbecides and further provides the advantage that the compositions are water-dispersible. Even further, the present esters provide greater microbecidal activity for the compositions than similar prior microbecidal compositions without the esters.

BACKGROUND OF THE INVENTION

In the above-identified earlier applications, it is disclosed that mono-esters of a twelve carbon atom aliphatic fatty acid and a polyol unexpectedly provide effective non-toxic microbecides. For example, the ester may be the lauric acid ester of glycerol or other polyol and the esterification taking place with a single hydroxy group. The ester cannot be the di-ester, or tri-ester. As noted in the parent applications, this result is quite unexpected, since the art, as cited in the earlier applications, indicates that activity of that nature should not be expected. This is based on the evidence in the art that substantial microbecidal activity is occasioned only with lower-chain fatty acids, i.e., below twelve carbon atoms, and that some derivatives of the acids reduce the microbecidal activity thereof. Experimental data has shown that when fatty acids are converted into surface-active compounds, only the ionic derivatives are active and the non-ionic derivatives are not only inactive but will inactivate other microbecides in the composition.

The invention of the parent applications was, in part, the discovery that the microbecidal properties of fatty acids and their derivatives vary in a non-uniform manner with chain length and that the results obtained with parent acids are not necessarily translatable to the derivatives of those acids. It was determined that only the defined polyol mono-esters of a twelve-carbon atom acid function most effectively as food-grade microbecides and that compositions with high amounts of these esters can be compounded and remain non-toxic.

Additionally, as the earlier applications point out, an important feature is that the defined esters are dissolvable or dispersible in an aqueous medium. Of course, that function is extremely important in food compositions, since these compositions very often are water-based systems.

Conventional food-grade "phenolic" microbecides, such as butylated hydroxy anisole (normally referred to as BHA), and 2,6-di-tert-butyl-4-methyl phenol (commonly referred to as BHT) are important additives for foods and food-grade materials. These compounds are also important antioxidants, but since their microbecidal properties are particularly considered herein, they will be referred to hereinafter as simply microbecides, for the sake of simplicity. The "phenolic" compounds are not substantially water-dispersible (they are lipophilic) and are normally applied in food compositions via a lipid base or vehicle. This requirement considerably complicates the application of those conventional food-grade microbecides to food compositions. Unfortunately, if BHA and BHT are compounded with non-ionic surfactants (which are hydrophilic), in order to aid dispersibility in water systems, the surfactants substantially inactivate those compounds.

Accordingly, the esters of the earlier applicantions provide a distinct advantage, as opposed to the more usual food-grade microbecides, such as BHA and BHT, in that they are water-dispersible and are more easily incorporated into aqueous food systems. It would be, however, of a substantial advantage in the art if those conventional phenolic microbecides could be compounded with a non-ionic surface-active agent to aid in the water-dispersibility and without significantly decreasing the activity of those microbecides. This would allow a more convenient application of the microbecides in both food-grade applications and non-food-grade applications.

OBJECTS OF THE INVENTION

It is, therefore, an object of the present invention to provide compositions wherein conventional microbecides, especially phenolic compounds, are compounded with a non-ionic surface-active agent which will allow water-dispersibility of those microbecides, while at the same time, the microbecidal activity thereof is not substantially reduced. It is a further object of the invention to provide those same compositions wherein the microbecidal activity is at least maintained and often increased rather than reduced, thus providing an unexpected synergism, i.e., the activity of the combined ingredients is greater than the additive activities of the separate ingredients. It is yet a further object of the invention to provide compositions of the foregoing nature which also includes a third active ingredient which potentiates the activity of the foregoing compositions. Lastly, it is an object of the invention to provide methods of use for such compositions.

BRIEF DESCRIPTION OF THE INVENTION

Accordingly, there is provided a microbecidal or microbiostatic combination comprising the active ingredients of at least one non-ionic surface-active mono-ester of a twelve-carbon atom aliphatic acid and a polyol and at least one microbecide. While any of the known microbecides may be used, it is preferred that the microbecide be selected from the group consisting of "phenolic" compounds, as defined hereinafter. The weight ratio of the microbecide to the ester is usually between 1:1 to 1:100. The ester is preferably a saturated acid ester and the polyol is preferably a glycol, e.g., glycerol, and, thus, a preferred ester is the mono-laurin (i.e., the 1-mono-laurin or the 2-mono-laurin, or mixtures thereof) of glycerol.

The foregoing composition is potentiated in its activity by the inclusion of ethylenediamine-tetraacetic acid or its alkali or alkaline earth salts. This compound is included in the combination of active ingredients, described above, in amounts, preferably, less than 20%, and more usually less than 15%. For food grade applications, it is preferred that the compound be contained in the combination of active ingredients in an amount less than 1%.

The composition may be in a form for applying to a material or living creature, e.g., birds and animals, including humans. For example, the composition may be applied to the skin of an animal or human. As a specific illustration, the composition has particular advantage in applying to teats of a mammal, such as a cow.

DETAILED DESCRIPTION OF THE INVENTION

The present invention is based upon several primary discoveries. A first and most-basic discovery is that the esters of the said earlier applications have the unexpected and unusual property of providing non-ionic surface-activity to a composition containing known microbecides, such as "phenolic" compounds, without inactivating those microbecides as was the normal experience in the art. Thus, a non-ionic vehicle or water-dispersible composition of those known microbecides may be provided.

A second basic discovery is that the esters of the earlier applications not only maintain the activity of the known microbecides, but provide a synergistic effect with known, and hereinafter identified, phenolic microbecides. When the phenolic microbecide is, inherently, a food-grade microbecide, compounding with the present esters to aid in water-dispersibility maintains that food-grade property, even within the ratios where the synergistic effect with the ester is obtained.

Lastly, the invention is based on the discovery that the ester and the phenolic microbecide may be compounded with ethylenediamine tetraacetic acid (EDTA) and an activation (potentiation) is achieved.

It is known, of course, that microbecides can form synergistic compositions and/or be potentiated in their effectiveness by the addition of other compounds. For example, combinations of organotins (e.g., tri-N-butyltin benzoate) and di-isobutyl phenoxy ethoxy ethyl di-methyl benzyl ammonium chloride monohydrate form such synergistic compositions, (see Organo Quaternary Ammonium Combinations as Disinfectants: R. J. Verdicchio; CSMA Proceedings, December 1969).

Shafiroff ("Synergism of Germicidal Compounds by Surface Active Agents": I. Shafiroff; *CSMA Proceedings;* May, 1961) reported that the combination of an amphoteric with a quaternary ammonium compound increased the activity of the quaternary over five times when tested against *P. fluorescens*. In addition, a synergism was observed with respect to *S. aureus* (gram positive) and *P. fluorescens* (gram negative) when parachloro-meta cresol and sodium hexadecyl-amino propionate were combined at ratios ranging from 2 parts phenol to 1 part of amphoteric to 5 parts of phenolic to 1 part of amphoteric.

On the other hand, non-ionic surface-active agents are known to have a general inactivating effect on microbecides. The noted exception seems to be the iodine-type microbecides. In this case, certain non-ionic surface-active agents are reported in combination with iodine without a reservation of decreased iodine activity. See, for example, U.S. Pat. No. 3,917,822. However, the usual case is that non-ionic surface-active agents deactivate microbecides. Thus, Beckett and Robinson (see Beckett, A. H.; Robinson, H. E.; *Soap, Perfumery and Cosmetics,* 31:1,99,1959) describe the effect of non-ionics as interfering with phenolic germicidal activity, while Moculeski (see "New Alkanolamide For Use With a Phenolic Germicide"; Moculeski, et al.; *CSMA Proceedings,* December 1960) reported that a modified alkanolamide combined with ortho-benzyl para-phenol and TSP/TSPP improved activity against *S. typhosa* and *S. choleraesuis*.

Heald (see "Useful Combinations of Anionic and Cationic Surfactants"; R. C. Heald; *American Perfumery and Aromatics;* April, 1960) reported that a non-ionic surfactant (alkyl phenol polyglycol ether) could be used at least at 10% of a total percentage when a cationic/anionic mixture was also present.

This problem of inactivation by non-ionic compounds has been particularly troublesome in connection with phenolic food-grade microbecides since it is important to keep the concentration of those microbecides as low as practical in food-grade composition. Thus, compounding those microbecides with a non-ionic surface-active agent in order to improve the water-dispersibility of the microbecides often results in such decreased activity of the microbecides as to render those microbecides impractical for many food applications. It can be appreciated that other than non-ionic surface-active agents can effect water-dispersibility of microbecides in foods without substantially decreasing the activity of the microbecides, but it will also be appreciated that those other surface-active agents (cationic/anionic) must be food-grade. As can, therefore, be further appreciated, the art has been faced with a very difficult problem in finding non-ionic surface-active agents which are acceptable for use foods and with food-grade materials but which do not unduly decrease the activity of microbecides used therein. The discovery that the present esters are capable of effecting non-ionic water-dispersibility of known microbecides and avoiding inactivation (actually providing a synergistic result in some cases) is a most surprising and unexpected discovery.

The esters of the present invention are the same as in the above-identified earlier applications. Thus, the esters must be a mono-ester of a twelve-carbon atom aliphatic acid and a polyhydric compound, i.e., a polyol. For food-grade applications, the acid and polyol must be non-toxic, i.e., must form a non-toxic ester. Food-grade applications include compounding in foods or a "food-grade" material. A food is defined as a digestible nutrient for animals, including humans. A food-grade material is defined as a non-essential ingestible substance (thus, excluding water), which may or may not be a nutrient for animals but is not considered a food, such as toothpaste, tooth powder, mouthwash, pharmaceuticals, detergents, soap and cosmetics, such as face creams, lipsticks, etc.

The acid of the ester is a twelve-carbon atom aliphatic mono-carboxylic acid. While the acid may be unsaturated (e.g., mono- or poly-unsaturated), considerably superior results are obtained with saturated acids. Further, while the acid may be branched, it is preferred that that acid be unbranched. Accordingly, the best mode of the acid is lauric acid.

The polyol of the ester may be any non-toxic polyhydroxylated compound, i.e., having two or more hydric moieties. For example, there may be used a glycol such as propylene glycol, or a polyalkylene glycol such as polyethylene glycol, or polypropylene glycol or a polyglycerol. Alternately, the polyol may be a non-toxic cellulosic ether, sucrose or inositol, etc. While the larger and more bulky polyols tend to increase water-solubility and affect other desirable properties, the esters prepared from bulky polyols are generally less active than the more simple and less bulky polyol esters. For these reasons, overall superior results are obtained with more simple polyols, especially those of less than 8 carbon atoms. Preferred polyols are trihydric aliphatic alcohols of less than 6 carbon atoms, such as glycerol.

Thus, the best mode of the invention is the monoester, where R is the lauric acid residue.

The concentration of the present ester in the food-grade composition and the range of ratios with the phenolic microbecide to the ester and the combination of food/ester, can vary widely. This is especially true since the esters may have no $LD_{50}$ (in the usual sense of the word). The parent acids may be FDA-GRAS materials. When a similar food-grade polyol is used, the esters could even be a food. However, the concentration of the present esters, generally, will be less than 30% by weight of the total food-grade composition, especially less than 20% or 15%, by weight, and usually from 0.001% to 2% by weight, the weight percentages being calculated on the basis of the weight of the free fatty acid.

The microbecides of the present invention are preferably "phenolic" compounds defined herein as having the general structure where $m$ is 0 to 3 (especially 1 to 3), $n$ is 1 to 3 (especially 1 to 2), $R_1$ is alkyl or alkenyl of up to 12 carbon atoms (especially up to 8 carbon atoms), and $R_2$ is H and alkyl or alkenyl of up to 8 carbon atoms (especially up to 6 carbon atoms), but where $R_2$ is H, $n$ is 1 or 2. Representative of such compounds are butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, and 4,6-di-tert-butyl-resorcinol. A preferred group of the phenolic microbecides is the phenol species having the general structure:

where $R_3$ is alkyl or alkenyl of up to 8 carbon atoms, and X is 0, 1, 2 or 3, especially where $R_3$ is butyl and partially tert-butyl, and especially the non-toxic members thereof.

The concentrations of the phenolic bactericides in the food-grade compositions may vary widely, but as little as 0.001%, based on the total weight of the composition, can be effective when the above-described esters are present within the above-noted ranges. However, it is preferred that the ratio of the phenolic to the ester be from about 1:1 to 1:100 and especially between 1:10 and 1:50, on a weight basis.

The above-noted concentrations of the phenolics are normally observed unless concentrated formulations for subsequent dilution are intended. On the other hand, the minimum concentration of the phenolic microbecide and the ester to provide a microbecidal or microbiostatic effective amount, e.g., a bactericidal or bacteriostatic effect, will vary with the particular application. For example, the present esters, alone, are effective microbecides in concentrations as low as less than a hundredth of a micromole per milliliter of composition when used in normal growth media. When used with the phenolic microbecides, the dilution may be at least one magnitude greater.

Of course, coloring agents, extenders, diluents, fillers, flavors, and the like, may be included, as is known in the art. The food-grade composition may be in the form of suspensions, pastes, solutions, jellies, creams and ointments, with or without conventional thickening agents such as carboxy methyl cellulose, gelatins, and the like. Likewise, sprays and mists may be prepared according to conventional formularies.

The compositions of the invention may be used on inanimate objects and materials, or on animals, including humans, for effecting microbecidal or microbiostatic action. For example, the compositions may effect bactericidal or fungicidal action on apparatus and utensils used in clinical procedures, in pharmaceutical manufacture, food-processing equipment, toothpaste, mouthwash, lipsticks, pharmaceuticals and food such as dairy products (milk, ice cream and cheese spreads), meat products (prepared meats and spreads) fruit and vegetable products (canned and frozen mushrooms, tomatoes, pears, etc.) and cereal products (breads, cakes, pastas and pies). If desired, the compositions may be used for non-food-grade applications such as for effecting bactericidal fungicidal or protozocidal action on the bodies of animals.

As disclosed the earlier applications, the present esters are bactericidal, per se, and according to the earlier applications, those esters may be used as the primary bactericide in a food or food-grade composition. With the present compositions, bactericidal esters of the earlier applications are combined in a synergistic manner with known food-grade phenolics to not only provide water dispersibility by virtue of the surface activity of the esters, but to preserve and, indeed, increase the activity of the known phenolic compounds. It can, therefore, be easily appreciated that the proper selection of a surface active agent to provide the foregoing results is of the upmost criticality. Further, as explained in the earlier applications, predictability of bactericidal properties for long chain fatty acid derivatives is hazardous at best. Chain length, unsaturation versus saturation, position of unsaturation, and the derivative of the ester can all produce widely different bactericidal results. To demonstrate the criticality of the selection of the particular fatty acid derivatives for present purposes, following Examples I – III compare the activity of homologous fatty acids, various polyhydric alcohol esters of the fatty acids, various fatty acid chain lengths and unsaturation, and mono-esters versus (poly) esters.

EXAMPLE I

In order to establish comparative bactericidal and fungicidal results with homologous fatty acids, a series of experiments was performed with thirty straight-chain fatty acids and derivatives thereof. Eight different gram-negative and twelve different gram-positive organisms, representing a very broad spectrum of organisms, were used in these experiments including the fungus Candida (a yeast). Additionally, fatty acids were chosen to show the effects of saturation versus unsaturation, in the fatty acid claim. Standard solutions of the fatty acids and their derivatives were prepared by first dissolving the weighed compounds in 1 to 2 ml of 95% ethanol and immediately pouring this solution into 200 ml of Tripticase Soy Broth. These lipid compounds which are insoluble in water and broth precipitated into very small crystals or droplets. The tubes containing the suspension were warmed to approximately 70° C and were then placed in an ultrasonic tank for further solubilization of the lipid derivatives.

Standard solutions (or suspensions) at 1,000 µg/ml were twofold serially diluted with additional broth to a concentration of 125 µg/ml. A 4-ml amount of each dilution was then quickly, and with constant agitation, dispensed into appropriately labeled screw-capped glass tubes (16 by 125 mm). The tubes were sterilized with steam at 15 psi for 15 minutes. After sterilization, all tubes were cooled and incubated overnight at 35° C to insure sterility.

If a compound was found to have inhibitory activity at concentrations lower than 125 µg/ml, the testing was continued to a final concentration of 1.5 µg/ml for each active compound. All compounds were compared on a molar (micromoles/milliliter) rather than on a mass basis. In the following lists of organisms used, those followed by a parenthetical number are registered with the American Type Culture Collection (ATCC); the remainder were isolates from Providence Hospital or Northland Laboratory.

Gram-positive organisms:
*Staphylococcus aureus, S. epidermidis, beta-hemolytic streptococci* (Group A and non-group A), group D streptococcus, *Bacillus subtilis* (6051), *Sarcina lutea* (9431), Micrococcus sp., *Candida albicans, Nocardia asteroids* (3308), Corynebacterium sp. (10700), and pneumococcus (63001).

Gram-negative organisms:
*Proteus vulgaris, P. mirabilis* (14273), *P. rettgeri* (9250), *Escherichia coli, Serratia marcescens* (13880), *Enterobacter-Klebsiella, Pseudomonas aeruginosa* (10145), and *Salmonella typhimurium*.

Strain differences within a genus were not significant by the present mode of testing.

One drop (0.04 ± 0.01 ml) of an 18-hr broth culture containing $10^7$ and $10^9$ organisms/ml was added to each dilution of the test compound, as well as to a tube of plain broth which served as the positive control. After inoculation, the contents of each tube were well mixed, and the tubes were incubated at 35° C in a 5% carbon dioxide + 95% oxygen atmosphere.

After 18 hours of incubation, the minimal inhibitory concentration (MIC) of each compound was determined for each microorganism. The MIC is defined as the lowest concentration of compound at which no microscopic evidence of growth was observed when turbidity of the inoculated broth dilutions was compared with control tubes. In those instances in which the test compound itself caused turbidity so that the MIC could not accurately be determined, a sample (0.015 ml) of the well-agitated broth was inoculated into a Trypticase Soy Agar plate containing 5% defibrinated sheep blood, incubated at 35° C, and examined after 18 hours for bacteriostatic and bactericidal end points. Only a one-tube difference between the bactericidal and bacteriostatic concentrations was normally observed.

To test the effects of the sterilization procedure on the stability of the unsaturated fatty acids, a control series was undertaken with 10mg each of oleic and linoleic acid. Each sample was dissolved in absolute methanol, and the volume was reduced in vacuo to 0.25 ml of the compound, and appropriate dilutions were made from this stock solution. The activity of these solutions was compared with that of sterilized controls.

As a comparison of effectiveness, a well-known surface-active agent, sodium lauryl sulfate, was used as a control. Such surface active agents are not active at concentrations > 1000 µg/ml.

Because insolubility of the compound is always a problem in testing lipid material, a control series was undertaken to investigate the effect of particulate suspensions on the bactericidal property. Particularly, the relationship of insolubility of a fatty acid to its biological activity was determined by a series of experiments in which lauric acid was used as the model compound as follows. A suspension of lauric acid, as well as a filtrate of the same suspension, was tested for antimicrobial activity. Bio Gel and Florisil were mixed with lauric acid-containing broth to remove particulate matter before it was filtered. Albumin (Miles Pentex, Fatty-Acid Free) to a final concentration of 1.1% was added to a suspension of lauric acid to study the effect of added protein on biological activity.

The data for nine gram-positive organisms and the yeast/fungus Candida are presented in Tables 1 and 3. Tables 2 and 4 give the range of activities, as well as the maximum concentration tested. Table 5 presents a comparison of the $C_{10}$ and $C_{12}$ free acids and their glyceryl derivatives, and Table 6 gives the corresponding ranges of activity.

Both methods of compound addition (pre- or post-sterilization) gave identical results except with linolelaidic acid. Repeat tests showed that the results for this fatty acid were variable and were dependent on the time, temperature, and pressure of autoclaving. For this compound, the results from the non-sterilized procedure were used.

While not shown in the tables, sodium lauryl sulfate was non-inhibitory for gram-negative organisms, and was inhibitory at 3.47 µmoles/ml, but not less than 0.347 µmole/ml, for gram-positive organisms. The compound is active in solution or in suspension.

Broth with laurate crystals removed was less inhibitory than non-filtered broth. For group A Streptococci, the results were 0.125 µmole/ml as compared to 1.0 µmole/ml (filtered). When Bio Gel and Florisil were used, the inhibition was reduced to greater than 0.99 µmole/ml. Albumin (0.1%) had no effect on the determination of the MIC under the conditions of the experiments.

As can be seen from Table 1, and as summarized by Table 2, there is a substantial difference in activity of the saturated acids. Thus, caproic acid, $CH_3(CH_2)_4COOH$, was not inhibitory at all, as was the case with stearic acid, $CH_3(CH_2)_{16}COOH$. Between this $C_6$ to $C_{18}$ saturated acid range, varying degrees of activity can be seen, but lauric acid is clearly the more active saturated acid.

The effects of unsaturation point up how unpredictable is the microbiological activity of these long chain acids. Not only does unsaturation have an effect (myristoleic/myristic and palmitoleic/palmitic) but the cis-/trans isomers have an effect (oleic/elaidic), as well as the specific amount of unsaturation (linoleic/linolenic/-linolelaidic acids) and the chain length with the unsaturation (arachidonic acid).

The unpredictability of the activity of long chain acids is further illustrated by Table 3, and as summarized by Table 4, where the corresponding alcohol, aldehyde, lower ester, higher ester, amine, amide, thiol and unsaturated analog of lauric acid are compared with lauric acid itself. As can be seen, only the amine and the amide showed activity comparable to the parent acid, but the compounds are not food-grade compounds.

As can also be seen from Tables 1 and 2, unsaturation appears to have an effect in the antibacterial activity of the longer chain fatty acids ($>C_{14}$), while there is little or no effect for the shorter chain fatty acids. However, unsaturation does appear to have an effect in the fungicidal activity of the shorter chain unsaturated esters. In addition the monoester is more fungicidal than the parent fatty acid.

Table 5 shows, as summarized in Table 6, a comparison between lauric acid and capric acid and their glyceride esters. Extremely striking results are obtained. For both the capric and lauric acids the mono-glycerides (1, or 2 mono-) are active while the di- (1,2 or 1,3) and tri-glycerides are inactive. This is most surprising and unexpected. Further, the mono-laurin was significantly more active than the mono-capric, with the sole exception of the streptococcus Group D organisms. In all other cases, the mono-laurin ranged from essentially as active to 5.5 times more active, a most surprising and unexpected result. Also note that essentially the 1-mono-laurin is as active as the 2-mono-laurin.

EXAMPLE II

This example compares the effects of polyhydric alcohol esters of the fatty acids.

Standard solutions (1000 μg/ml) of three fatty acids and polyglycerol esters thereof were prepared as described in Example I. Also sucrose esters were prepared by transferring the weighed compounds (0.2 gm. dissolved in 1 ml absolute methanol) into 200 ml of sterile Trypticase Soy Broth (TSB). These standard solutions (1000 μg/ml) were twofold serially diluted with additional sterile broth to a concentration of 125 μg/ml. A 3.8 aliquot of each dilution was aseptically delivered into sterile screw-capped culture tubes. All tubes were incubated overnight at 36° C to insure sterility. The microorganisms used in this example were the same as those used in Example I.

The inoculum, 0.05 ml of an 13-24 hour TSB culture (approximately $10^9$ organisms/ml) was asceptically delivered into all dilutions of the compounds, mixed well, and incubated at 36° C. A tube of inoculated broth without the compound served as a positive control and an uninoculated set of dilutions incubated along with the test dilutions, served as a negative control.

After 18-hours of incubation, the Minimal Inhibitory Concentration (MIC) of each compound was determined for the organisms tested. In those cases in which the test compound itself caused turbidity, an aliquot (0.015 ml) of the mixed broth was inoculated onto an agar plate and incubated at 36° C for examination, as described in Example I. The control procedure of Example I was also repeated. The lauric, capric, and oleic acids were used as internal controls and for comparison to Example I. The minimal inhibitory concentrations (μmole/ml) for the compounds studied are given in Tables 7 and 8.

Table 7 shows the MIC's for the polyglycerides and compares the same with the free acid form. The tri-and hexaglycerol monocaprates have greater inhibition in some cases than the free acid form but the spectrum is not as wide as the free acid form. They do not inhibit the Staphylococci or Group D Strep.

The tri-, hexa-, and decaglycerol monolaurates have less inhibition than the free acid form. These polyglycerol monolaurates do not inhibit the Staphylococci or Group D Strep.

Triglycerol oleate has no activity at the concentration tested while the free acid form has very limited activity.

Table 8 compares various sucrose esters with lauric acid. Sucrose esters, except for the laurate, are more active in some cases than the free acid form, but their antimicrobial spectrum of activity is more limited. None of the tested sucrose esters inhibit *Staphylococcus aureus* or Group D Strep. Sucrose palmitate is the only ester which inhibits *S. epidermis* and *Sarcina*. Table 9 shows the analytical results of the composition of the sucrose esters, with the exception of sucrose caprate.

While not shown in the tables, two other lauric acid derivatives were tested against six organisms. Thus, α-hydroxylaurate was active against Group A Strep (0.23 μmole/ml and *Nocardia asteroides* (4.63 μmoles/ml). Methyl, α-hydroxylaurate was inhibitory to S. aureus, Group A Strep, and *Saccharomyces cerevisiae* (0.54 μmole/ml) and *Nocardia asteroides* (4.34 μmoles/ml). Neither compound was inhibitory for Group D Strep and *E. coli*.

EXAMPLE III

From Examples I and II, it can be seen that fatty acid chain length and unsaturation can have effects on the bactericidal activity of the fatty acids. This example shows the activity in more detail.

Examples I and II show that the Group A β-hemolytic Streptococci organisms give results typical of the results of all of the organisms for a particular fatty acid or derivative. Therefore, to simplify the testing procedure, this typical organism is used in this Example.

Similarly to Examples I and II, solutions of potassium soaps of certain fatty acids were inoculated with 0.05 ml. of an 18-hour broth culture of a virulent Group A β-hemolytic Streptococci. Acid concentrations after the second dilution, (pH 7.6) had no appreciable effect on the pH of the media. The minimal inhibitory concentration (MIC) in μmoles/ml for each acid was determined after an overnight incubation of the acid and microorganism at 35° C in a 5% $CO_2$ + 95% $O_2$ atmosphere in a manner similar to Examples I and II.

Figure 1:
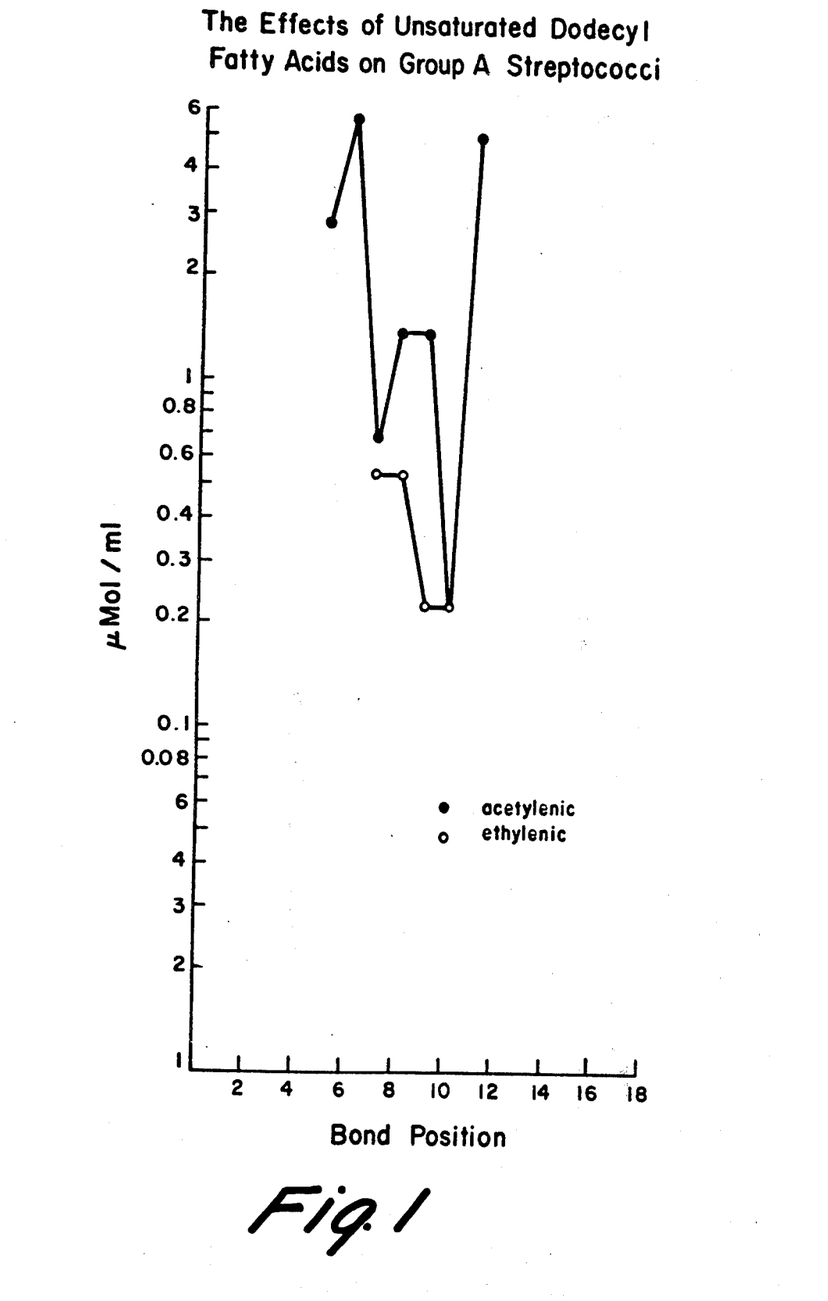
FIG. 1 shows a comparison between ethylenic and acetylenic unsaturation of twelve-carbon atom fatty acids.

The results for the $C_{12}$ acids are presented in FIG. 1. Generally, the ethylenically-unsaturated acids were more active toward the Group A Streptococci than the corresponding acetylenically-unsaturated acids. The greatest difference between these two types of unsaturation is found with the $\Delta^9$ isomer. For both types of unsaturation, the $\Delta^{10}$ isomer was the most active.

Figure 2:
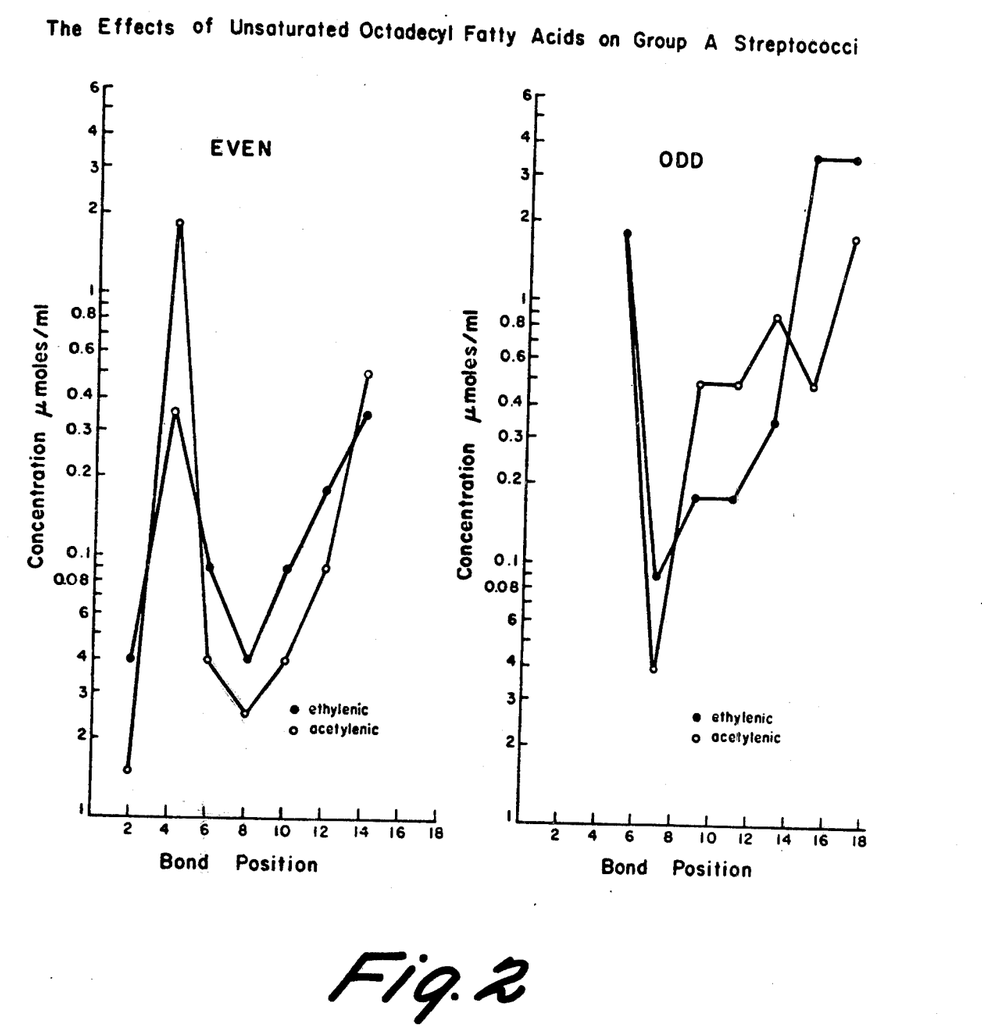
FIG. 2 shows the unpredictable effect of unsaturation by way of eighteen carbon atom fatty acids.

By comparison, as shown in FIG. 2, the $C_{18}$ acids were more active toward Group A Streptococci than the $C_{12}$ acids. This data is divided into two homologous series of isomers, i.e., odd vs. even carbon chain length. For each series, the ethylenically-unsaturated acids are generally less active than acetylenically-unsaturated acids. However, since the data for $\Delta^6$, $\Delta^8$, $\Delta^{10}$, $\Delta^{12}$, $\Delta^{14}$, $\Delta^{17}$ isomers represent only one tube difference in the testing procedure, it is not necessarily significant. Differences between ethylenically- and acetylenically-unsaturated acids at positions $\Delta^4$ and $\Delta^{15}$ are, however, significant. Greater inhibitory activity for both types of unsaturation is noted when the unsaturation is in the $\Delta^2$, $\Delta^7$ or $\Delta^8$ positions.

The effect of a second double bond and its positional isomers is seen from 18:2 acids. These acids are more active than the 18:1 series. For comparative purposes, individual monoenoic isomers (two) which have unsaturation in similar positions to the dienoic molecule, are compared to the dienoic acid, i.e., the $\Delta^{9,12}$ 18:2 is compared to the $\Delta^9$ 18:1 and the $\Delta^{12}$ 18:1. The differences are listed in Table 10. In such a comparison, the activity of the 18:2 is always greater than the component 18:1 isomers. Usually the more unsaturated fatty acids are 8–15 fold more toxic.

EXAMPLE IV

Figure 3:
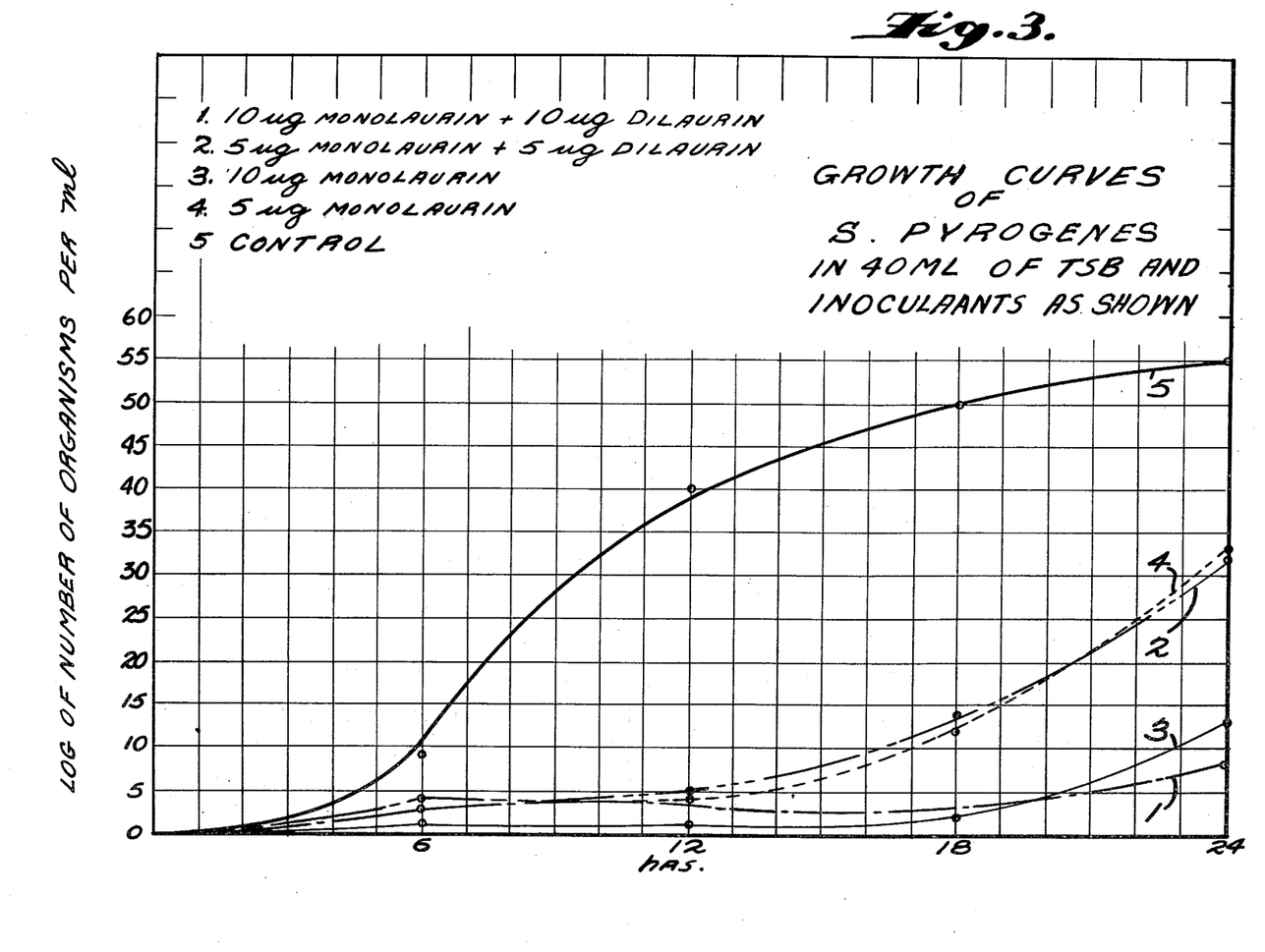
FIG. 3 shows the growth curve of *S. pyogenes* in comparing glycerol mono-esters and diesters of lauric acid.

To a series of containers is added 40 ml of Trypticase Soy Broth and 0.5 ml of *streptococcus pyogenes* ($10^8$ organisms/ml). To respective containers are added the following: (1) 10 μg of glycerol 1-mono-laurin and 10 μg of glycerol dilaurin; (2) 5 μg of glycerol 1-mono-laurin and 5 μg of glycerol dilaurin; (3) 10 μg of glycerol 1-mono-laurin; and (4) 5 μg of glycerol 1-mono-laurin; and (5) a control without any additives. The rate of growth of the S. pyogenes was followed for 24 hours at 6 hour intervals by reading the optical density of the cultures at 550 mm in a spectrophotometer. The results are shown in FIG. 3. As can be seen, the test with 1-mono-laurin alone gave essentially the same results as when tested with equal amounts of dilaurin. Thus, the dilaurin is essentially inactive, while the mono-laurin is responsible for all antimicrobial activity.

From the foregoing Examples, it can be seen that predictability of biological activity for long-chain fatty acids and derivatives thereof is exceedingly low. Chain length, saturation or unsaturation (as well as the type of unsaturation and position thereof) and the type of derivative (as well as variations in the degree of substitution of its derivative, e.g. mono- versus di- or tri-) can cause significant variations in activity toward one organism and other variations towards groups of different organisms.

Such unpredictable results have probably been the reason for the contradictory conclusions and statements in the art as to the activity or lack of activity of long-chain fatty acids and derivatives thereof. These contradictory results and conclusions have discouraged attempts at using these materials as antimicrobial agents.

Thus, these experimental results point out the superior esters within the broad range of esters. The mono-laurin derivatives provide unique combinations of properties, i.e., food-grade, active toward a wide spectrum of both gram-positive and gram-negative organisms, yeast and protozoan active at low concentrations. Thus, the mono-laurins constitute a distinct class of compounds with unique and unexpected superior results and constitute the preferred esters of the invention.

EXAMPLE V

The essential procedure of Example I was followed with a series of phenolic compounds, with the exception that the test method was conducted on a mass (μg/ml) basis rather than a molecular (mol/ml) basis of the foregoing tests, since the long established phenol-coefecient test is on a mass rather than molecular basis. Additionally, a different but closely related group of organisms were used in this test, in order to give a complete representative span on gram-negative, gram-positive and fungus organisms. Additionally, the phenolic derivatives chosen for test purposes include a number of derivatives which are presently accepted by the FDA as food-grade phenolic microbicides. The results of these tests are shown in Table 11. Also note that phenol itself is shown in the table as a standard for comparison purposes, although phenol itself is not as active as other of the derivatives. For example, compare the activity of phenol with BHA and it will be seen that BHA is significantly more active. Similarly, the butylated phenols are more active than BHA, while the butylated alkyl phenols, including BHT, are not as active. For example, BHT compares in activity to phenol itself. This is further elucidated in Table 12 where the above procedure was repeated, but with butylated alkyl phenol of varying alkyl chain length, as defined in Table 12. Note that the chain length $C_1$ (which is BHT) is not quite as active as the ethyl derivative ($C_2$), but that the activity again decreases with chain length and the $C_4$ to $C_{10}$ derivatives are even less active. While not shown in the table, the composition is also quite active against *Streptococcus mutans* (ATCC 10441) which is indicated in oral carries.

From the foregoing, it will be observed that BHA is the representative of the more active FDA accepted food grade phenolic microbicides. This compound, along with BHT, are also the most important compounds commercially. Thus, BHA forms the best mode of the invention and will, therefore, be used in the following illustration of the synergistic feature of the present invention.

EXAMPLE VI

The same procedure of Example V was repeated but with combinations of mono-laurin (GML). The results are summarized in Table 13. As before, the gram-negative, gram-positive and fungi are separated by space in the table for easy identification. Considering the results in the table, it will be observed that the glycerol mono-laurin (GML) is essentially inactive toward a gram-negative organisms. It will also be noted that BHA has fairly low activity toward the gram-negative organisms. Combinations of the mono-laurin and BHA also exhibit essential inactivity toward the gram-negative organisms. On the other hand, it will be dramatically observed that while the mono-laurin has substantial activity toward the gram-positive and considerably better activity than the BHA organisms, the combination of the mono-laurin and the BHA gives a surprising high activity. Thus, the combination of the more active mono-laurin with the less active BHA produces activity far greater than either the mono-laurin or BHA alone. This, of course, is classical synergism. It should also be noted that this high activity carries through to the lowest BHA content measured (0.01%).

Synergism is even further grammatically illustrated in the case of the fungi. Here, the mono-laurin is substantially inactive while the BHA shows acceptable but clearly not superior activity. However, combining only the moderately active BHA and the substantially inactive mono-laurin provides a highly active synergistic combination. It is, therefore, quite surprising that a mildly active microbicide (BHA) can be combined with a substantially inactive fungicide (mono-laurin) and produce a highly active combination.

As noted hereinbefore, it is a further feature of the invention that the present synergistic combination can be additionally activated by the presence of ethylenediamine tetraacetic acid (EDTA). Based on the weight of the combination of the present ester and microbicide, the EDTA may be present in amounts from as little as 0.001% to as high as 5%, although that range will more normally be between 0.005% and 3% and more usually between 0.01% and 1%. This surprising effect is illustrated by the following examples.

EXAMPLE VII

The procedure of Example V was repeated with combinations of glycerol mono-laurin (GML) and ethylenediamine tetraacetic acid (EDTA) as the calcium salt and in combination with BHA. The results of these experiments are shown in Table 14. Here again, it will be noted that the principal activity of the glycerol mono-laurin is in connection with the gram-positive organisms. The EDTA, alone, has essentially no activity toward either the gram-positive, gram-negative or fungi and, again, BHA has very little activity against the gram-positive but acceptable activity against the selected group of gram-negative organisms and reasonable activity against fungi. A combination of the glycerol mono-laurin and the EDTA provides a very substantial improvement in the activity of the combination toward gram-positive organisms and the combination of glycerol mono-laurate, EDTA and BHA gives most surprising results in that it is not only extremely active against gram-positive organisms, but then becomes extremely active against the fungi and some of the tested gram-negative organisms.

EXAMPLE VIII

The procedure of Example 1 was repeated, but in this case the absolute reading of the various combinations were taken at 60 minutes and reported as that reading. Table 15 shows the results of those experiments. Note from the table that the base line for the experiment is shown as 0.0% and has a 60 minute reading of 2.3 × $10^6$ CFU. It will also be noted that on a 1% basis of mono-laurin increasing the concentration of BHA from 0.1% to 0.5% gives nearly two orders of magnitude increase in activity on the 60 minute reading scale. Also, it will be noted that at the 0.1% BHA concentration, the inclusion of 1.0% EDTA increase the activity by factor of only about 2 and similar results can be seen from comparing the activity of the compositions containing 0.5% BHA and 0.5% BHA + 1% EDTA. Thus, while the EDTA does have an activating influence on the combination of mono-laurin and BHA, this activating influence is not as remarkable as the influence of the mono-laurin on the BHA or vice-versa.

Actually, a syngeristic result is also obtained with combinations of glycerol mono-laurin and EDTA without any further microbicide therein. This is illustrated by the following example.

EXAMPLE IX

The procedure of Example 5 was repeated with the organism shown in Table 16. Here again, note the low level of activity of either GML, EDTA or BHT alone or in combination against gram-positive organisms. Also note the essential lack of activity of GML, EDTA, or BHT alone against the fungi. However, as far as the gram-positive organisms are concerned, the combination of GML and EDTA gives improved results and the activity of that combination against fungi is increased by more than a factor of 10. The combination of GML, EDTA and BHT does not effect any activity against gram-positive organisms, and does not substantially increase the activity of that combination against gram-positive organisms, as opposed to the combination of GML and EDTA, but the latter combination does increase the activity of fungi. Accordingly, EDTA does have a property of activating the GML, principally, against the fungi and has the further property of improving that activity in combination with BHT.

The potentiation activity of EDTA for GML is further demonstrated in Table 17. That table is the result of experiments carried out according to the procedure of Example 5 but with the organisms shown therein. Note that as the amount of EDTA increases from 0 to about 5 to 10,000, the activity of the GML steadily increases. This should be understood in the context of the activity of EDTA, as shown in that table which is, for all practical purposes, inactive. For easy comparison purposes, compare the activity of GML (0 amount of EDTA) with EDTA (0 amount of GML) in the extreme left and extreme right hand columns respectively with the activity of the combination in the column labelled "10,000". Thus, EDTA does have a very pronounced potentiation effect for GML, whether or not the GML includes other microbicides.

The following example further demonstrates the effects of combinations of the present mono-laurin, BHA, BHT and EDTA.

EXAMPLE X

The procedure of Example 5 was repeated with the percentages shown in Table 18. The results of this experiment are recorded in the 60 minute reading. Note that the base line (0.0% of all nominated ingredients) is 2.2 × $10^{6CFU}$. In this experiment, for the 60 minute reading, as opposed to the MIC value of the other experiments, the addition of 1% BHT and 1% EDTA did not increase the 60 minute reading effectiveness substantially. However, when BHA is included in the combination, i.e. either with EDTA or without EDTA or with BHT and EDTA, the activity increases to less than 1,000 (1,000 organisms represent the limit of detection in this system).

From the data discussed above, it can be easily seen that the mono-laurin provides an effective vehicle for known microbicides. This vehicle is of a non-ionic nature and, contrary to the experience in the art, allows this non-ionic emulsification and/or water dispersion without inactivation of the microbicide. Further, with phenolic microbicides, a synergistic effect with the mono-laurin is observed. While this effect varies with the phenolics, the combination with BHA is surprisingly effective. BHT, the other more important commercial phenolic, is, inherently, less active than BHA, but nevertheless is considerably more potentiated by the present mono-laurin. Thus, the present invention gives wide latitude in compounding known microbicides with a non-ionic surface active vehicle and in some cases provides a synergistic effect therebetween. It should also be understood, as explained above, that it is the mono-laurin as opposed to the di- tri- and poly- esters which is effective commercially available esters for normally mixtures of mono- di- tri- and poly- esters and these normally commercially available esters will not be acceptable for the present invention. In any event, the mono-laurin ester should comprise at least 80% of the mixture of esters. Otherwise, the deactivating influence of contaminating di- tri- and poly- esters or esters of other than lauric acid will substantially over-shadow the benefits of the mono-laurin that may be contained in that combination. Thus, the mono-ester should be at least 80% pure.

It should also be understood, as is the case with most microbicides, that the pH has an affect on the activity thereof. The present combination should be used at pH between about 4 and 10, more preferably between 5 and 8 and appropriate buffers and the like may be included in the combination for that purpose. These buffers, among other things, may include conventional salt buffers. It is important to understand in this regard, that salt buffers may be used even when EDTA is included in the combination, since contrary to the teachings in the art, EDTA is not simply a chelating agent which some salts would cause interference, but is, indeed, a potentiating and synergistic effecting compound for the mono-laurin and phenolic microbicides. Thus, it is not necessary to avoid salt buffers, as would be expected from the prior art teachings of EDTA in similar compositions.

The present compositions can be formulated into a wide variety of end products, both foods and food-grade material, as well as non-food-grade material. Because of the extremely high microbidical activity of the synergistic combinations, those combinations are particularly effective as antibacterial scrubs and the like. The following examples will illustrate formulations for final products.

EXAMPLE XI

A surgical scrub is prepared by heating 10 parts of glycerol mono-laurate, 1 part BHA and 1 part EDTA to a temperature of about 50°–70° C where the mixture forms a melt. To this melt is added 100 parts of water heated to 50°–70° C. After stirring, the mixture is gradually cooled in an ice bath to achieve proper particle size and micro-crystalline state, which gives a relatively stable suspension. The scrub is easy to apply to the hands and produces a feeling somewhat akin to the feeling of an emollient. It is not harsh or unpleasant. When tested in the manner of Example V, the scrub was determined to have high activity against the gram-positive and gram-negative organisms of Table 13 and has an effective killing time of 5 minutes. Additionally, the composition was achieved against Klebsiella BT-101-76.

EXAMPLE XII

A hospital baby wash was prepared in the same manner as the surgical scrub of Example XI, but with the addition of 5% lactic acid thereto. The 60 minute reading of the baby wash was $6.4 \times 10^4$. The addition of the lactic acid improves the antimicrobal effect and provides additional emollients for the baby wash.

EXAMPLE XIII

A teat-dip was prepared in the matter described in Example XI, except that 70 parts of heated water is used. After cooling to room temperature 30 parts of isopropanol is added to provide an alcoholic solution. This combination is effective against both gram-positive and gram-negative organisms and has a killing time of five minutes. Thus, the teat-dip is most effective for combating mastitis in cows.

EXAMPLE XIV

Three conventionally-formulated mouthwashes were prepared and the mouthwashes were tested by a modified phenol coefficient test. Additionally, the same formulations were prepared but with the inclusion of either 0.5% or 1.0% of the glycerol monolaurin ester, and either 0.01% or 0.50% of BHA.

The first-tested mouthwash was composed of 5% alcohol, zinc chloride, methanol, and conventional aromatics to provide a red mouthwash.

A second mouthwash was prepared with 15% alcohol, cetylpyridinium chloride, oil of peppermint, boric acid, and methanol to provide a blue mouthwash.

18½% alcohol and cetylpyridinium chloride was used to provide a green mouthwash.

The red, blue and green mouthwashes are conventionally produced and commercially-marketed mouthwashes.

Each of the red, blue and green mouthwash, when tested against Staph aurelus No. 43 with the modified phenol coefficient test and showed the number of viable organisms as $1.44 \times 10^6$, $1.85 \times 10^4$ and $2 \times 10^2$. In all cases, however, with the inclusion of the mono-ester and BHA, the number of organisms was zero, with the exception of the red mouthwash containing 0.5% of the ester and 0.01% of BHA, where the number of organisms was < 50. The number of organisms was measured at 120 minutes.

EXAMPLE XV

The conventionally-formulated dermatological inert carrier was formed with the monolaurin ester of glycerol and with 0.1% E.D.T.A., in one case, and with 5% (e.g., 0.5–20%) lactic acid, in a second case. A stasis test was performed. In this test, the forearm of test subjects was wrapped under Saran wrap for 24 hours and, thereafter, the densities of aerobes per square centimeter were determined and are reported below as the geometric means for five test subjects. Similarly, a cidal test was performed. Here, again, the forearm of the test subjects was wrapped with Saran wrap, but, in this case, for 48 hours, in order to expand the flora. Thereafter, the test agents were applied to the test subjects under occlusion for 24 hours. The geometric means for five test subjects are shown below. In both tests, a control of the inert dermatological carrier is also included.

|  | CONTROL | 1% ESTER | 1% ESTER 0.1% EDTA | 1% ESTER 0.1% EDTA 5.0% LACTIC ACID |
|---|---|---|---|---|
| STAIS: | 562,000 | 278,000 | 870,000 | 314 |
| CIDAL: | 873,000 | 218,000 | 181,000 | 79 |

EXAMPLE XVI

In a manner similar to that described in Example V, the effectiveness of certain food-grade microbecides are compared with mono-esters in an agar dilution method. The very favorable results may be noted from Table 19.

TABLE 1
MIC OF 15 FATTY ACIDS (μMol/ml)

| Organism<br>Compound | Pneumo-cocci | Strepto-coccus Group A | Strepto-coccus β-hemolytic Non-A | Coryne-bacteria | Nocardia asteroides | Micro-cocci | Candida | S. aureus | S. epider-midis | Strepto-coccus Group D |
|---|---|---|---|---|---|---|---|---|---|---|
| Caproic | NI* | NI | NI | NI | NI | NI | NI | NI | NI | NI |
| Caprilic | NI | NI | NI | NI | NI | NI | NI | NI | NI | NI |
| Capric | 1.45 | 1.45 | 2.9 | 1.45 | 1.45 | 2.9 | 2.9 | 2.9 | 2.9 | 5.8 |
| Lauric | .062 | 0.124 | 0.249 | 0.124 | 0.124 | 0.624 | 2.49 | 2.49 | 2.49 | 2.49 |
| Myristic | 0.218 | 0.547 | 2.18 | 0.437 | 0.547 | 0.547 | 4.37 | 4.37 | 2.18 | 4.37 |
| Myristoleic | 0.110 | 0.110 | 0.110 | 0.055 | 0.110 | 0.220 | 0.552 | 0.441 | 0.441 | 0.441 |
| Palmitic | 0.48 | 3.9 | 3.9 | 1.9 | NI | 1.9 | NI | NI | 3.9 | NI |
| Palmitoleic | 0.024 | 0.098 | 0.049 | 0.049 | 0.049 | 0.049 | 0.491 | 0.983 | 0.491 | 0.491 |
| Stearic | NI | NI | NI | NI | NI | NI | NI | NI | NI | NI |
| Oleic | NI | 1.77 | NI | NI | NI | NI | NI | NI | NI | NI |
| Elaidic | NI | NI | NI | NI | NI | NI | NI | NI | NI | NI |
| Linoleic | 0.044 | 0.089 | 0.089 | 0.044 | 0.089 | 0.089 | 0.455 | NI | NI | NI |
| Linolenic | 0.179 | 0.35 | 0.35 | 0.179 | 0.488 | 0.488 | NI | 1.79 | NI | NI |
| Linolelaidic | NI | NI | NI | NI | NI | NI | NI | NI | NI | NI |
| Arachidonic | NI | NI | NI | NI | NI | NI | NI | NI | NI | NI |

*Not inhibitory at the concentrations tested (1.0 μg/ml or 3 to 6.0 μmol/ml).

TABLE 3
MIC OF DODECYL COMPOUNDS (μMol/ml)

| Organism<br>Compound | Pneumo-cocci | Strepto-coccus Group A | Strepto-coccus βhe Molytic Non-A | Coryne-bacteria | Nocardia asteroides | Micro-cocci | Candida | S. aureus | S. epider-midis | Strepto-coccus Group D |
|---|---|---|---|---|---|---|---|---|---|---|
| Lauric acid | 0.062 | 0.124 | 0.249 | 0.124 | 0.124 | 0.624 | 2.49 | 2.49 | 2.49 | 2.49 |
| Lauryl alcohol | 0.067 | 0.067 | 0.271 | 0.135 | 0.135 | 0.135 | 0.135 | 0.271 | 0.135 | 5.4 |
| Lauryaldehyde | 0.136 | 0.136 | 0.136 | 0.136 | 0.136 | 0.54 | 0.136 | 0.272 | 0.272 | NI |
| Methyl laurate | — | 4.6 | NI | 4.6 | 4.6 | 2.3 | 4.6 | NI | NI | 4.6 |
| Lauryl acetate | NI | NI | NI | NI | NI | NI | NI | NI | NI | NI |
| Cholesterol laurate | NI | NI | NI | NI | NI | NI | NI | NI | NI | NI |
| Dodecylamine HCl | 0.056 | 0.056 | 0.112 | 0.028 | 0.112 | 0.112 | 0.112 | 0.112 | 0.112 | 0.112 |
| Lauryl N,N-dimethylamide | 0.054 | 0.054 | 0.109 | 0.054 | 0.054 | 0.109 | 0.109 | 0.109 | 0.109 | 0.109 |
| 1-Dodecane-thiol | NI | NI | NI | NI | NI | NI | NI | NI | NI | NI |
| Dodecanedioic acid | NI* | NI | NI | NI | NI | NI | NI | NI | NI | Ni |

*NI — Not inhibitory at the concentrations tested.

TABLE 2
MIC RANGES (μMol/ml)

| Compound | Range | Max. tested |
|---|---|---|
| Caproic | NI | 10 |
| Caprilic | NI | 7.8 |
| Capric | 1.45 – 5.8 | 5.8 |
| Lauric | 0.062 – 2.49 | 4.9 |
| Myristic | 0.218 – 4.37 | 4.37 |
| Myristoleic | 0.055 – 0.552 | 4.4 |
| Palmitic | 0.48 – NI | 3.9 |
| Palmitoleic | 0.024 – 0.983 | 3.93 |
| Stearic | NI | 3.5 |
| Oleic | 1.77 – NI | 3.54 |
| Elaidic | NI | 3.54 |
| Linoleic | 0.044 – NI | 3.56 |
| Linolenic | 0.179 – NI | 3.59 |
| Linolelaidic | NI | 3.59 |
| Arachidonic | NI | 3.2 |

TABLE 4
MIC Ranges of Dodecyl Compounds (μMol/ml)

| Compound | Range | Max. tested |
|---|---|---|
| Lauric acid | 0.062 – 2.49 | 4.9 |
| Lauryl alcohol | 0.067 – 5.4 | 5.4 |
| Lauryaldehyde | 0.136 – NI | 5.4 |
| Methyl laurate | 2.3 – NI | 4.6 |
| Lauryl acetate | NI | 4.38 |
| Cholesteryl laurate | NI | 1.76 |
| Dodecylamine HCl | 0.028 – 0.112 | 4.5 |
| Lauryl N,N-dimethylamide | 0.054 – 0.109 | 4.39 |
| 1-Dodecane-thiol | NI | 4.94 |
| Dodecanedioic acid | NI | 4.3 |

TABLE 5
MIC Comparison (μMol/ml)
Free Acid Form vs. Glyceride Form

| Organism<br>Compound | Pneumo-cocci | Strep. Grp.A. | Strep. β-hemo. Non-A | Coryne-bacteria | Nocardia asteroides | Micro-cocci | Candida | Staph aureus | Staph epid. | Strep. Grp.D. |
|---|---|---|---|---|---|---|---|---|---|---|
| Capric acid | 1.45 | 1.45 | 2.90 | 1.45 | 1.45 | 2.90 | 2.90 | 2.90 | 2.90 | 5.80 |

TABLE 5-continued
MIC Comparison (μMol/ml)
Free Acid Form vs. Glyceride Form

| Organism | Pneumo-cocci | Strep. Grp.A. | Strep. β-hemo. Non-A | Coryne-bacteria | Nocardia asteroides | Micro-cocci | Candida | Staph aureus | Staph epid. | Strep. Grp.D. |
|---|---|---|---|---|---|---|---|---|---|---|
| 1-mono-caprin | 0.10 | 0.20 | 0.20 | 0.20 | 0.50 | 0.10 | 1.00 | 1.00 | 1.00 | 2.00 |
| 1,3-dica-prin | | | — | NO INHIBITION (>3.30)* | — | | 2.49 | 2.49 | 2.49 | 2.49 |
| Lauric acid | 0.06 | 0.12 | 0.25 | 0.12 | 0.12 | 0.62 | 2.49 | 2.49 | 2.49 | 2.49 |
| 1-mono-laurin | 0.09 | 0.05 | 0.09 | 0.05 | 0.09 | 0.09 | 0.09 | 0.09 | 0.09 | >3.63* |
| 2-mono-laurin | —** | 0.09 | 0.19 | 0.19 | 0.19 | 0.09 | — | 0.19 | 0.09 | >3.63* |
| 1,2-di-laurin | | | — | NO INHIBITION (>2.18)* | — | | | | | |
| 1,3-di laurin | | | — | NO INHIBITION (>2.18)* | — | | | | | |
| trilaurin | | | — | NO INHIBITION (>1.56)* | — | | | | | |

*No inhibition [Max.] tested listed.
**Not tested

TABLE 6
MIC Ranges of Free Acid Form with Glyceride Form (μ/Mol/ml)

| Compound | Range | Max. Treated |
|---|---|---|
| Capric Acid | 1.45 – 5.8 | 5.8 |
| 1-mono-caprin | 0.1 – 2.0 | 4.04 |
| 1,3-dicaprin | NI | 3.3 |
| Lauric acid | 0.062 – 2.49 | 4.9 |
| 1-mono-laurin | 0.045 – NI* | 3.63 |
| 1,3-dilaurin | NI | 2.18 |
| Trilaurin | NI | 1.56 |

*Highly active on all organisms except streptococcus Group D which is non-inhibitory

TABLE 7
MIC Comparison (μMol/ml)
Free Acid Form vs. Polyglyceride Form

| Organism | Strep. Grp. A | Strep. β-hemo. Non-A | Corne-bacteria | Micro-cocci | Sarcina | Staph aureus | Staph epider. | Strep. Grp. D |
|---|---|---|---|---|---|---|---|---|
| Compound | | | | | | | | |
| Capric acid | 1.45 | 2.90 | 1.45 | 2.90 | — | 2.90 | 2.90 | 5.80 |
| Triglycerol monocaprate | 0.15 | 0.63 | 0.32 | 1.26 | 2.50 | >2.50* | >2.50* | >2.50* |
| Hexaglycerol monocaprate | 0.19 | 0.79 | 0.39 | 0.79 | >1.58* | >1.58* | >1.58* | >1.58* |
| Lauric acid | 0.12 | 0.25 | 0.12 | 0.62 | 2.49 | 2.49 | 2.49 | 2.49 |
| Triglycerol monolaurate | 0.29 | 0.59 | 0.24 | 0.29 | 1.18 | >2.36* | >2.36* | >2.36* |
| Hexaglycerol monolaurate | 0.19 | 0.38 | 0.38 | 0.38 | >1.52* | >1.52* | >1.52* | >1.52* |
| Decaglycerol monolaurate | 0.26 | 0.53 | 0.53 | 0.53 | >1.06* | >1.06* | >1.06* | >1.06* |
| Oleic acid | 1.77 | | — | | NO INHIBITION (>3.54)* | — | | |
| Triglycerol oleate | | — NO INHIBITION (>1.98)*- | | | | | | |

*No inhibition [Max.] tested listed.

TABLE 8
MIC (μMol/ml)
Effectiveness of Sucrose Esters[1]

| Organism | Pneumo-cocci | Strep. Grp.A | Coryne-bacteria | Nocardia asteroides | Micro-cocci | Sarcina | Staph. epider. |
|---|---|---|---|---|---|---|---|
| Compound | | | | | | | |
| Lauric acid | 0.06 | 0.12 | 0.12 | 0.12 | 0.62 | 2.49 | 2.49 |
| Sucrose laurate | 0.12 | 0.03 (.12) | 0.47 (.23) | 0.47 (1.90) | 1.90 | >1.90* | >1.90* |
| Sucrose caprate | 0.06 | 0.06 | 0.25 | 0.25 | 1.00 | >2.00* | >2.00* |
| Sucrose myristate | 0.23 | 0.05 (.11) | 0.11 (.11) | 0.23 (.11) | 0.23 | >1.84* | >1.84* |
| Sucrose palmitate | 0.05 | 0.10 (.20) | 0.43 (.26) | 0.43 (>1.72*) | 0.26 | 0.43 | 0.86 |
| Sucrose elaidate | 0.20 | 0.20 | 1.64 | 0.20 | 0.82 | >1.64* | >1.64* |
| Sucrose oleate | 0.05 | >1.64*(.41) | >1.64*(>1.64*) | 0.41 (.21) | 0.21 | >1.64* | >1.64* |
| Sucrose | 0.05 | 0.41 (.82) | >1.66*(1.66) | 0.41 (1.66) | 0.82 | >1.66* | >1.66* |

TABLE 8-continued

| Organism | Pneumo-cocci | Strep. Grp.A | MIC (µMol/ml) Effectiveness of Sucrose Esters[1] Coryne-bacteria | Nocardia asteroides | Micro-cocci | Sarcina | Staph. epider. |
|---|---|---|---|---|---|---|---|
| linoleate | | | | | | | |

*No inhibition, [Max.] tested listed
[1]Gram positive organisms not inhibited by sucrose esters are *Staph. aureus, Bacillus subtillis* and Grp. D *Strep.*

TABLE 9

Analytical Results of the Samples Sucrose Esters

| Sample | Sucrose Ester, % | Composition % Mono- | Di- | Tri- | Degree of Substitution | Composition of Fatty Acid | |
|---|---|---|---|---|---|---|---|
| Sucrose laurate | 90.3 | 58.3 | 34.0 | 7.7 | 1.39 | $C_{12}$ min. | 99% |
| Sucrose myristate | 89.3 | 61.5 | 33.6 | 4.9 | 1.34 | $C_{14}$ min. | 94% |
| Sucrose palmitate | 87.1 | 52.4 | 6.4 | 11.1 | 1.45 | $C_{16}$ min. | 93% |
| Sucrose | 67.9 | 60.2 | 32.8 | 7.0 | 1.35 | $C_{18:1}$ | 75.5% |
| | | | | | | $C_{18:2}$ | 11.5% |
| | | | | | | $C_{18}$ | 7.3% |
| | | | | | | $C_{16}$ | 5.2% |
| | | | | | | $C_{14}$ | 0.5% |
| Sucrose linoleate | 72.0 | 48.7 | 36.0 | 15.4 | 1.51 | $C_{18:2}$ | 52.6% |
| | | | | | | $C_{18:1}$ | 24.9% |
| | | | | | | $C_{18:3}$ | 7.9% |
| | | | | | | $C_{18}$ | 5.3% |
| | | | | | | $C_{16}$ | 8.2% |
| | | | | | | $C_{20}$ | 0.9% |

TABLE 10

Comparison of Ethylenic 18:2 vs. 18:1 MIC's Against Group A Strep. (µMol/ml)

| DIENOIC | MONOENOIC | MIC | DIFFERENCE |
|---|---|---|---|
| $\Delta^{9,12}$ | | 0.01 | |
| | $\Delta^{12}$ | 0.18 | 0.17 |
| | $\Delta^{9}$ | 0.18 | 0.17 |
| $\Delta^{8,12}$ | | 0.02 | |
| | $\Delta^{12}$ | 0.18 | 0.16 |
| | $\Delta^{8}$ | 0.04 | 0.02 |
| $\Delta^{7,12}$ | | 0.02 | |
| | $\Delta^{12}$ | 0.18 | 0.16 |
| | $\Delta^{7}$ | 0.09 | 0.07 |
| $\Delta^{6,12}$ | | 0.01 | |
| | $\Delta^{12}$ | 0.18 | 0.17 |
| | $\Delta^{6}$ | 0.09 | 0.08 |
| $\Delta^{5,12}$ | | 0.02 | |
| | $\Delta^{12}$ | 0.18 | 0.16 |
| | $\Delta^{5}$ | 1.77 | 1.75 |
| $\Delta^{6,12}$ | | 0.01 | |
| | $\Delta^{6}$ | 0.09 | 0.08 |
| | $\Delta^{12}$ | 0.18 | 0.17 |
| $\Delta^{6,11}$ | | 0.02 | |
| | $\Delta^{6}$ | 0.09 | 0.07 |
| | $\Delta^{11}$ | 0.18 | 0.16 |
| $\Delta^{6,10}$ | | 0.01 | |
| | $\Delta^{6}$ | 0.09 | 0.08 |
| | $\Delta^{10}$ | 0.09 | 0.08 |

TABLE 11

MIC VALUES (µg/ml) FOR CERTAIN PHENOLOLIC DERIVATIVES

| Compound Organism | 2,5-di-tert-butylphenol | 3,5-di-tert-butylphenol | 4,6-di-tert-butylresorcinol | 3,5-di-tert-butyl-2,6-dihydroxbenzoic acid | 3(2)-tert-butyl-hydroxy-anisole (BHA) |
|---|---|---|---|---|---|
| *Escherichia coli* | >1,000 | >1,000 | >1,000 | >1,000 | >1,000 |
| *Pseudomonas aeruginosa* | >1,000 | >1,000 | >1,000 | >1,000 | >1,000 |
| *Strepococcus mutans* | 7.80 | 15.60 | 7.80 | 31.25 | 62.50 |
| *Streptococcus agalactiae* | 15.60 | 31.25 | 15.60 | 15.60 | 125 |
| *Staphylococcus aureus* | 62.50 | 31.25 | 15.60 | 31.25 | 125 |
| *Corynebacterium sp.* | 7.80 | 15.60 | 7.80 | 15.60 | 62.50 |
| *Nocardia asteroides* | 7.80 | 15.60 | 7.80 | 15.60 | 125 |
| *Candida albicans* | >1,000 | 62.50 | 62.50 | 500 | 125 |
| *Saccharomyces cereyisiae* | 62.50 | 62.50 | 15.60 | 500 | 125 |

Dilutions tested: 1,000 500 250 125 62.50 31.25 15.60 7.80 4.00

TABLE 12

MIC VALUES (µg/ml) FOR CERTAIN PHENOLOLIC DERIVATIVES

| | BHT | | | | Chain Length* | |
|---|---|---|---|---|---|---|
| Organism | $C_1$ | $C_2$ | $C_4$ | $C_6$ | $C_8$ | $C_{10}$ |
| *Eschericia coli* | NI | NI** | NI | NI | NI | NI |
| *Pseudomonas aeruginosa* | NI | NI | NI | NI | NI | NI |

TABLE 12-continued

MIC VALUES (μg/ml) FOR CERTAIN PHENOLOLIC DERIVATIVES

| | BHT | | Chain Length* | | | |
|---|---|---|---|---|---|---|
| Organism | $C_1$ | $C_2$ | $C_4$ | $C_6$ | $C_8$ | $C_{10}$ |
| Streptococcus faecalis (Group D) | NI | 2,500 | NI | NI | NI | NI |
| Streptococcus pyogenes | 1,000 | 1,000 | 5,000 | NI | NI | NI |
| Staphylococcus aureus | NI | 5,000 | NI | NI | NI | NI |
| Corynebacterium sp. | 100 | 1,000 | 1,000 | 5,000 | 5,000 | 5,000 |
| Nocardia asteroides | 1,000 | 500 | 500 | 5,000 | 5,000 | 5,000 |
| Candida albicans | NI | NI | NI | NI | NI | NI |
| Saccharomyces cerevisiae | NI | NI | NI | NI | NI | NI |

**Highest dilution tested: 5,000 μg/ml

TABLE 13

MIC VALUES (μg/ml) FOR GLYCEROL MONO-LAURIN AND BHA

| | Compound | | | | |
|---|---|---|---|---|---|
| Organism | GML | BHA | GML plus BHA (.05%) | GML plus BHA (.025%) | GML plus BHA (.01%) |
| Escherichia coli | >1,000 | 500 | >1,000 | >1,000 | >1,000 |
| Pseudomonas aeruginosa | >1,000 | >1,000 | >1,000 | >1,000 | >1,000 |
| Streptococcus mutans | 31.25 | 62.50 | <7.80 | <7.80 | <7.80 |
| Streptococcus agalactiae | 15.60 | 62.50 | <7.80 | <7.80 | <7.80 |
| Staphylococcus aureus | 31.25 | 125 | <7.80 | <7.80 | <7.80 |
| Nocardia asteroides | 15.60 | 62.50 | <7.80 | <7.80 | <7.80 |
| Candida albicans | >1,000 | 125 | <7.80 | <7.80 | <7.80 |
| Saccharomyces cerevisiae | <1,000 | 125 | <7.80 | <7.80 | <7.80 |

TABLE 14

MIC VALUES (μg/ml) FOR GLYCEROL-MONO-LAURIN, ETHYLENE-DIAMINE-TETRAACETIC ACID (EDTA)

| Organism Compound | GML | EDTA ($N_2$Ca salt) | BHA | GML plus EDTA (.05%) | GML plus EDTA (.05%) plus BHA (.1%) |
|---|---|---|---|---|---|
| Escherichia coli | >1,000 | <1,000 | 500 | >1,000 | <7.80 |
| Pseudomonas aeruginosa | >1,000 | >1,000 | >1,000 | >1,000 | >1,000 |
| Streptococcus mutans | 31.25 | 500 | 62.50 | <7.80 | <7.80 |
| Streptococcus agalactiae | 31.25 | >1,000 | 62.50 | 15.60 | <7.80 |
| Staphylococcus aureus | 31.25 | >1,000 | 125 | 15.60 | <7.80 |
| Nocardia asteroides | 7.80 | 1,000 | 62.50 | <7.80 | <7.80 |
| Candida albicans | >1,000 | >1,000 | 125 | 500 | <7.80 |
| Saccharomyces cerevisiae | 1,000 | >1,000 | 125 | 31.25 | <7.80 |

TABLE 15

EFFECT OF MONOLAURIN AND BHA CONCENTRATIONS ON BACTERICIDAL PROPERTIES

| Percent Monolaurin | Percent BHA | Percent EDTA ($Na_2$) | 60 Minute Reading, CFU (Coloney Forming Units) |
|---|---|---|---|
| 0.0 | 0.0 | 0.0 | $2.3 \times 10^6$ |
| 1.0 | 0.5 | 1.0 | $<1.0 \times 10^3$ |
| 1.0 | 0.1 | 1.0 | $1.7 \times 10^5$ |
| 1.0 | 0.5 | — | $1.0 \times 10^3$ |
| 1.0 | 0.1 | — | $3.6 \times 10^5$ |

TABLE 16

MIC VALUES OF GML/EDTA AND BHT ALONE AND IN COMBINATIONS

| Organism Compound | GML | EDTA | BHT | GML plus EDTA (0.1%) | GML Plus EDTA (0.1%) plus BHT (0.1%) |
|---|---|---|---|---|---|
| Escherichia coli | >1,000 | >1,000 | >1,000 | >1,000 | >1,000 |
| Pseudomonas aeruginosa | >1,000 | >1,000 | >1,000 | >1,000 | >1,000 |
| Streptococcus faecalis (Group D) | >1,000 | >1,000 | >1,000 | >1,000 | 1,000 |
| Streptococcus pyogenes | 10 | 1,000 | 1,000 | <10 | <10 |
| Staphylococcus aureus | 1,000 | >1,000 | >1,000 | 100 | 100 |
| Corynebacterium sp. | 10 | >1,000 | 100 | <10 | <10 |
| Nocardia asteroides | 10 | 1,000 | 1,000 | <10 | <10 |
| Candida albicans | >1,000 | >1,000 | >1,000 | 100 | 100 |
| Saccharomyces cerevisiae | 1,000 | 1,000 | >1,000 | 100 | <10 |

TABLE 17

EFFECT OF EDTA ON MIC OF GML (μg/ml)

| Organism | EDTA 0 | 125 | 250 | 500 | 1,000 | 5,000 | 10,000 | EDTA |
|---|---|---|---|---|---|---|---|---|
| Escherichia coli | >10,000 | >10,000 | >10,000 | >10,000 | >10,000 | >10,000 | >10,000 | >10,000 |
| Pseudomonas aeruginosa | >10,000 | >10,000 | >10,000 | >10,000 | >10,000 | 100 | <10 | 5,000 |
| Strephtococcus faecalis (Group D) | >10,000 | >10,000 | >10,000 | >10,000 | 1,000 | <10 | <10 | 5,000 |
| Staphylococcus aureus | 1,000 | 1,000 | 1,000 | 500 | 100 | <10 | <10 | 5,000 |
| Streptococcus pyogenes | <10 | <10 | <10 | <10 | <10 | <10 | <10 | 1,000 |
| Corynebacterium sp. | <10 | <10 | <10 | <10 | <10 | <10 | <10 | 1,000 |
| Nocardia asteroides | <10 | 100 | <10 | <10 | <10 | <10 | <10 | 500 |
| Candida albicans | >10,000 | 500 | 500 | 100 | 100 | 100 | 100 | 5,000 |
| Saccharomyces cerevisiae | 1,000 | 500 | 100 | 100 | <10 | <10 | <10 | 1,000 |

TABLE 18

MONOLAURIN, BHA, AND BHT AS AN ANTIMICROBIAL AGENT

| Percent Monolaurin | Percent BHA | Percent BHT | Percent EDTA | 60 Minute Reading |
|---|---|---|---|---|
| 0.0 | 0.0 | 0.0 | 0.0 | 2.2 × 10⁶ |
| 1.0 | 1.0 | — | 1.0 | >1.0 × 10³ |
| 1.0 | — | 1.0 | 1.0 | 9.5 × 10⁵ |
| 1.0 | 1.0 | — | — | >1.0 × 10³ |
| 1.0 | — | — | — | 9.7 × 10⁵ |
| 1.0 | 0.5 | 0.5 | 1.0 | >1.0 × 10³ |

TABLE 19

MIC VALUES (μg/ml) FOR CERTAIN FOOD-GRADE MICROBECIDES TESTED BY AGAR DILUTION METHOD

| Test materials | Staphylococcus aureus | Bacillus subtilis | Escherichia coli | Pseudomonas aeruginosa | Aspergillus niger | Canadida albicans |
|---|---|---|---|---|---|---|
| Palmitoleic acid sodium salt | 15.60 | 500 | >1,000 | >1,000 | >1,000 | >1,000 |
| Glycerine-1-monolaurin | 39 | 39 | >2,500 | >2,500 | >2,500 | >2,500 |
| Sorbic acid | 1,000 | 1,000 | 1,000 | 2,000 | 1,000 | 1,000 |
| Phenol | 1,250 – 2,500 | 1,250 | 2,500 | 1,250 | 1,250 | 1,250 – 2,500 |
| Thimerosal | 0.78 | 0.39 | 1.60 | 6.30 – 12.50 | 0.10 | 0.10 – 0.20 |
| Methyl paraben | 5,000 | 5,000 | 2,500 | 5,000 | 2,500 | 2,500 |
| Propyl paraben | 2,500 | 2,500 | 5,000 | >10,000 | 2,500 | 2,500 |

What is claimed is:

1. A microbecidal or microbiostatic composition having included therein effective amounts of the combination active ingredients of:
   1. at least one microbecidal surface-active mono-ester of a twelve carbon atom aliphatic acid and a polyol; and
   2. at least one active phenolic microbecide.

2. The composition of claim 1 wherein the acid of the said mono-ester is a saturated acid and the ester is a polyhydric alcohol ester.

3. The composition of claim 1 wherein the ester and microbecide form a synergistic combination and the weight ratio of the microbecide to the ester is between 1:1 and 1:100.

4. The composition of claim 2 wherein the alcohol is glycerol.

5. The composition of claim 4 wherein the 1 or 2 ester is the mono-laurin.

6. The composition of claim 1 wherein the composition is in a form for applying to the skin of an animal or human.

7. The composition of claim 6 wherein the composition is in a form for applying to the teats of a cow.

8. The composition of claim 1 which also includes ethylenediamine tetraacetic acid or a salt thereof.

9. The composition of claim 8 wherein the ratio of mono-ester to the ethylenediamine triacetic acid is between 100:1 to 10:1.

10. The composition of claim 1 wherein the combination of microbecide and mono-ester is water-dispersible.

11. The composition of claim 1 wherein the composition is contained in a food or food-grade composition.

12. The composition of claim 1 wherein the phenolic microbecide is a food-grade compound.

13. The composition of claim 12 wherein the compound is selected from the group consisting of butylated hydroxy anisole and di-tert-butyl-methoxy-phenol.

14. The composition of claim 1 in the form of a toothpaste or toothpowder composition.

15. The composition of claim 1 in the form of a mouthwash composition.

16. The composition of claim 1 in the form of a face cream or lipstick composition.

17. The composition of claim 1 in the form of a a pharmaecutical composition.

18. The composition of claim 1 in the form of a suspension, paste, jelly, cream, ointment or spray composition.

19. The composition of claim 12 in the form of a toothpaste, toothpowder or mouthwash composition.

20. The composition of claim 12 in the form of a face cream or lipstick composition.

21. The composition of claim 12 in the form of a pharmaceutical composition.

22. The composition of claim 12 in the form of a suspension, paste, jelly, cream, ointment or spray composition.

23. A method for effecting a microbecidal action in a composition comprising adding thereto a microbecidally or microbiostatically-effective amount of a combination of active ingredients of:
   1. at least one surface-active mono-ester of a twelve carbon atom aliphatic acid and a polyol; and
   2. at least one active phenolic microbecide.

24. The method of claim 23 in which the composition is a food or food-grade composition.

25. The method of claim 23 wherein the ester is of a glycol ester.

26. The method of claim 23 wherein the ester is of a polyhydric alcohol ester of a saturated acid and the ester and microbecide form a synergistic combination and the weight ratio of microbecide to the ester is between 1:1 and 1:100.

27. The method of claim 23 wherein the ester is the 1 or 2 mono-laurin.

28. The method of claim 23 wherein the composition is in a form for applying to the skin of an animal or human.

29. The method of claim 23 wherein the composition is in a form for applying to the teats of a cow.

30. The method of claim 23 wherein the said composition includes ethylenediamine tetraacetic acid, or a salt thereof.

31. The method of claim 30 wherein the ratio of the mono-ester to the ethylenediamine tetraacetic acid is between 100:1 to 10:1.

32. The method of claim 26 in which the composition is a food or food-grade composition.

33. The method of claim 26 wherein the ester is a 1 or 2-mono-laurin.

34. The method of claim 23 wherein the phenolic compound is selected from the group consisting of butylated hydroxy anisole and di-tert-butyl-methoxy-phenol.

* * * * *

UNITED STATES PATENT AND TRADEMARK OFFICE
CERTIFICATE OF CORRECTION

PATENT NO. : 4,067,997
DATED : January 10, 1978
INVENTOR(S) : Jon J. Kabara

It is certified that error appears in the above-identified patent and that said Letters Patent are hereby corrected as shown below:

Line bridging columns 5 and 6, line 68, delete "partially" and insert --particularly--.

Column 12, line 63, delete "organisms".

Columns 22 and 23, in Table 12, in title delete word "PHENOLOLIC" and insert --PHENOLIC--

Signed and Sealed this

Ninth Day of May 1978

[SEAL]

Attest:

RUTH C. MASON
Attesting Officer

LUTRELLE F. PARKER
Acting Commissioner of Patents and Trademarks